United States Patent
Säfström

(10) Patent No.: US 6,257,885 B1
(45) Date of Patent: Jul. 10, 2001

(54) METHOD AND AN INSTRUMENT FOR FILLING AN OCCLUSAL SURFACE OF A MOLAR OR PREMOLAR

(76) Inventor: Kent Säfström, Skolgatan 16, Märsta (SE), 195 34

( * ) Notice: Subject to any disclaimer, the term of this patent is extended or adjusted under 35 U.S.C. 154(b) by 0 days.

(21) Appl. No.: 09/496,195

(22) Filed: Feb. 2, 2000

(30) Foreign Application Priority Data

Nov. 26, 1999 (SE) .................................................. 9904292

(51) Int. Cl.⁷ .................................................. A61C 9/00
(52) U.S. Cl. .................................................. 433/40; 433/215
(58) Field of Search .................................. 433/34, 40, 39, 433/214, 37, 215

(56) References Cited

U.S. PATENT DOCUMENTS

| | | | |
|---|---|---|---|
| 853,984 | * | 5/1907 | Lauderdale .............................. 433/40 |
| 2,237,926 | * | 4/1941 | Cooley .................................... 433/40 |
| 4,718,849 | * | 1/1988 | Von Weissenfluh et al. .......... 433/39 |
| 4,881,898 | * | 11/1989 | Harvey, Sr. et al. ................... 433/34 |
| 5,332,390 | * | 7/1994 | Roselini ................................. 433/34 |
| 5,807,101 | * | 9/1998 | Scalzo ................................... 433/39 |
| 5,890,896 | * | 4/1999 | Padial ................................... 433/40 |

* cited by examiner

Primary Examiner—Todd E. Manahan
(74) Attorney, Agent, or Firm—Jacobson Holman, PLLC

(57) ABSTRACT

There is provided an instrument which carries a tool (52) that is transparent to light used to harden or cure a composite material. A matrix band (30) is placed around a molar or premolar and the composite material is placed on the tooth inwardly of the matrix band. The tool has a shaping surface (53) that has a shape and size corresponding to the mesio-occlusal shape or disto-occlusal shape of a corresponding molar or premolar of average shape and size. The tool (52) is pressed hard against the mesio or distal part of the matrix band (30) and against a neighboring tool whilst the tool (52) is, at the same time, pressed down in the composite material preferably so as to achieve contact with at least one of the cusps of the occlusal surface. The composite is light-hardened whilst the tool (52) is held in place.

18 Claims, 1 Drawing Sheet

METHOD AND AN INSTRUMENT FOR FILLING AN OCCLUSAL SURFACE OF A MOLAR OR PREMOLAR

BACKGROUND OF THE INVENTION

1. Field of the Invention

The present invention relates to a tooth filling or tooth repairing process and an instrument for shaping and curing tool composite material in a temporary cavity that has been established by a matrix band placed around the occlusal part of a molar or premolar to be filled or repaired.

2. Description of the Related Art

The occlusal surface of a premolar or molar is normally repaired by applying a thin flexible, normally metallic, matrix band around the tooth with the aid of a matrix holder, so that the band will project beyond the surface of the tooth and a filling of composite material is built-up in one or more layers (increments) in the cavity defined by the matrix band and the tooth, said layer or layers each having a thickness of 2–3 mm. The layer or layers is/are light-hardened. The soft, or non-hardened, composite filling can be pressed down in the cavity with the aid of a narrow, generally pin-like tool which is ball-shaped at its tip and carried on one end of an instrument handle, so that the tool, whose cross-sectional area is much smaller than the area of the occlusal surface, can be pushed down into the composite and used to press the composite out to the peripheral walls of the cavity. The instrument is translucent to light that will harden the composite material, so as to enable the composite to be hardened at the pointed part of the tool.

The ball-shaped tip of the tool can be used to form grooves in the composite material on the occlusal surface prior to hardening said composite material, with the purpose of recreating a topography similar to the topography of a normal occlusal surface of a molar or premolar.

One problem with this known technique is that it is difficult to shape the composite material on the occlusal surface to a correct topography with the aid of the tool of said instrument. Another problem resides in the difficulty in establishing good contact between the filled tooth and its neighboring teeth. Furthermore, the work involved in shaping a correct occlusal surface is relatively laborious.

SUMMARY OF THE INVENTION

The object of the present invention is to provide a method and an instrument with which the aforesaid problems can be eliminated either completely or partially.

Another object of the invention is to enable the occlusal surface to be given an attractive standard shape in one and the same working step and to establish a filling which has harder and better contact with neighboring teeth, so as to save time on the part of the dentist and to enable a better and neater filling to be made.

BRIEF DESCRIPTION OF THE DRAWINGS

The invention will now be described in more detail by way of example, with reference to the accompanying drawing.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
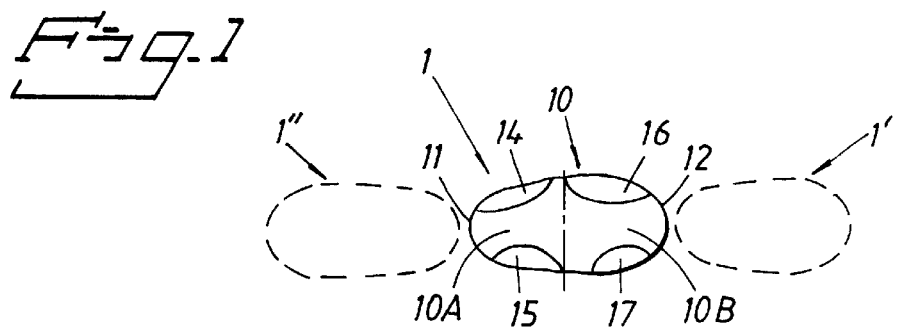
FIG. 1 is a schematic view from above of the occlusal surface of a molar and its neighboring teeth in the tooth row.
Figure 2:
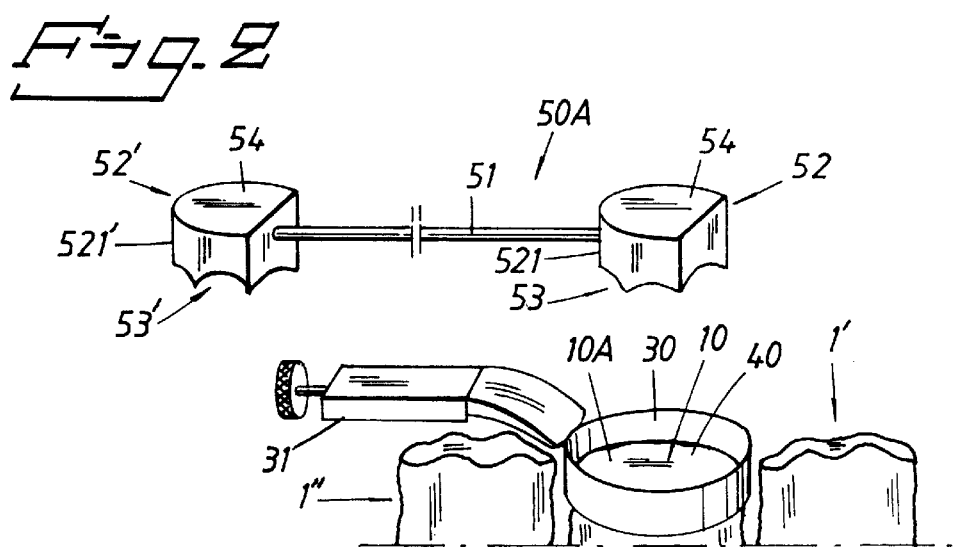
FIG. 2 is a perspective illustration of the tooth row according to FIG. 1 and shows a matrix band applied with a matrix holder on the molar, and also shows a relevant instrument.

FIG. 1 shows an occlusal surface 10 of a molar 1, and also shows the teeth 1' and 1" immediately adjacent said molar. The occlusal surface has a mesio-occlusal edge bead 11, a disto-occlusal edge bead 12, lingual-palatinal cusps 14, 16 and buccal cusps 15, 17. FIG. 2 shows that a matrix-holder band 30 is tightened around the circumference of the molar 1 with the aid of a matrix holder 31, so that the band 30 and the occlusal surface 10 to be filled or repaired form a cavity 40. A light-hardenable composite filling is applied in the cavity 40. The composite material is shaped with the aid of an instrument 50A that includes a handle 51 which carries a tool 52. The tool 52 may have a planar shape corresponding to the average or standard shape of the mesio-occlusal part 10A of the molar 1. One end 53 of the tool has a topography corresponding to the topography of the mesio-occlusal part 10A of the molar. The opposite end surface 54 of the tool may be generally parallel with the surface 53. The surfaces 53, 54 may have generally the same area and the tool 52 may be generally cylindrical in shape. A light source (no shown) can be connected to the surface 54 of the tool, so that the transparent tool 52 will conduct composite hardening light to the occlusal shaping surface 53 of the tool.

The dentist applies the instrument 50A so that the shaping surface 53 (the patrix surface) of the tool enters the cavity 40, wherewith the dentist brings the mesial part 521 of the tool 54 against, the band 30 in a direction towards the neighboring tooth 1" while, at the same time, pressing down the surface 53 of the tool 52 in the still soft composite material. Thus, the instrument and its tool 52 are pressed hard against the mesial part of the matrix band and against the neighboring tooth 1" whilst, at the same time, pressing the shaping surface 53 of the tool 52 down into the composite material so as to achieve contact with one or both cusps 14, 15, if possible. The tool 52 is held pressed while hardening the composite material with light delivered through the transparent tool. Surplus composite material is then removed in a conventional manner and the vertical extension of the resultant occlusion surface is checked. A check is also made to ensure that the filling will allow correct lateral movement between mutually coacting teeth.

FIG. 2 also shows an instrument handle 51 which carries at its other end a tool 52' whose construction is principally the same as that of the tool 52 but which includes a shaping surface 53' that has a planar form adapted to the disto-occlusal part 10B of the molar. The disto-occlusal part of the occlusal surface 10 adjacent the neighboring tooth 1' can now be filled in the aforedescribed manner with the aid of the tool 52'.

The shaping surface 53, 53' of the tool 52, 52' covers the area from the mesio-occlusal edge bead and the disto-occlusal edge bead to roughly the center of the occlusal surface and extends up to the edge of the lingual-palatal cusps 14, 16 and the buccal cusps 15, 17.

The instrument illustrated in FIG. 2 can be used to treat molars in the upper jaw and the lower jaw, where one tool can be used to shape a mesio-occlusal filling and the other tool can be used to shape a disto-occlusal filling.

Figure 3:
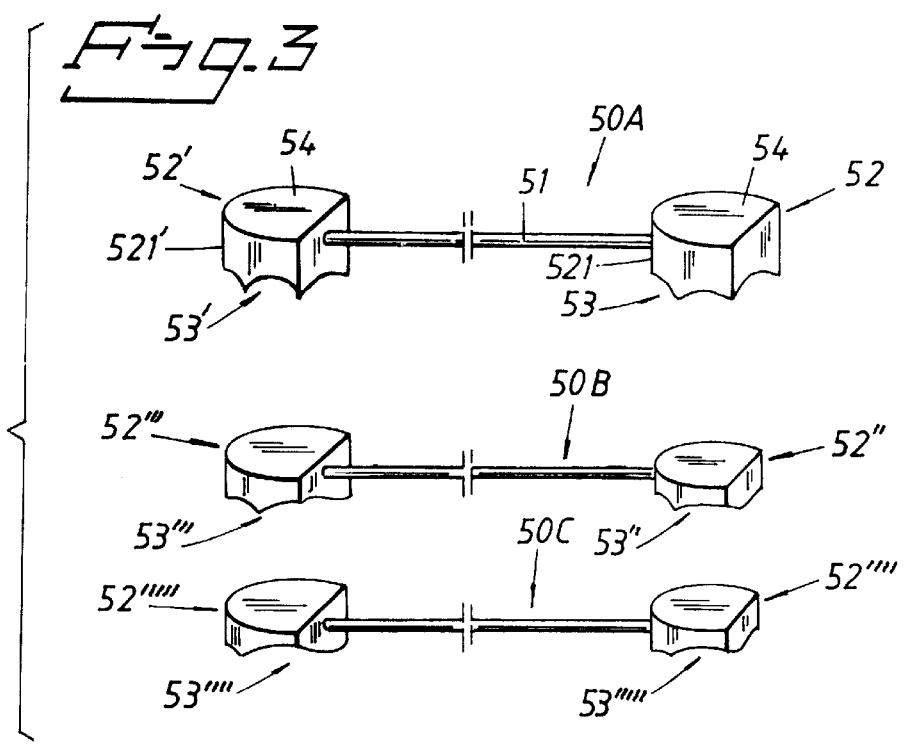
FIG. 3 illustrates schematically a number of instruments with which the inventive method can be carried out.

A similar tool 50B (FIG. 3) can include in a corresponding manner a handle 51 that carries two tools 52", 52'" which have shaping surfaces 53" and 53'" for respective mesio-occlusal and the disto-occlusal surfaces of the premolars in the upper jaw.

A third, similar instrument 50C (FIG. 3) has respective surfaces 53"" and 53""' for shaping respective mesio-occlusal and disto-occlusal surfaces on the premolars of the lower jaw.

The person skilled in this art will have access to information relating to standard topography and standard sizes of the molar occlusal surfaces and will be able to design the patrix surfaces 53 on the inventive tools on the basis of this information. Should information relating to dimensions and topographies of the occlusal surfaces not be available, the average person skilled in this art will have the capability of making a series of measurements to evaluate a "normal" or "average" occlusal surface for human molars and premolars, and then design the surfaces of the tools on the inventive instrument in accordance therewith.

The instrument tools 52 may conveniently be made of polypropylene, for instance Moplen®. Such material has effective transparency for the light used to harden or cure the most common composite materials and also enables the tools to be used several times. The handle 51 of the instrument may also be made of this polypropylene material. The instrument 50A, 50B or 50C may be injection-molded as a one-piece structure. The choice of polypropylene for manufacture of the instrument for instance, enables the instrument to be autoclaved by conventional methods and to be reused several times before becoming worn out. Polypropylene plastic is environmentally friendly, in other words can be dumped without needing to comply with special rules and regulations, and can also be reused.

What is claimed is:

1. An instrument for shaping and curing tool composite material in a temporary cavity that has been established by a matrix band placed around an occlusal part of a molar to be filled or repaired with the aid of a matrix holder, said instrument comprising a handle and a tool which is carried by said handle and which is transparent to light used for hardening or curing the composite material, said tool having a shaping surface with a shape that corresponds to one of a mesio-occlusal surface or a disto-occlusal surface of a molar or premolar of average shape and size generally corresponding with the molar or premolar to he filled or repaired.

2. The instrument according to claim 1, wherein the tool is generally cylindrical between the shaping surface and an opposing end surface generally parallel therewith.

3. The instrument according to claim 1, wherein the handle carries a tool at each end, wherein one tool has a shaping surface corresponding to the mesio-occlusal surface of a premolar or molar of average shape and size, corresponding generally to the premolar or molar to be filled or repaired, and the other tool has a shaping surface corresponding to the disto-occlusal surface of a premolar or molar of average shape and size, corresponding generally to the premolar or molar to be filled or repaired.

4. The instrument according to claim 3, wherein the instrument is contained in an instrument kit which includes a first instrument having two tools for mesio-occlusal and disto-occlusal surfaces, respectively, of molars in the upper and lower jaws, a second instrument having two tools for mesio-occlusal and disto-occlusal surfaces, respectively, of upper jaw premolars, and a third instrument having two tools for mesio-occlusal and disto-occlusal surfaces, respectively, of lower jaw premolars.

5. The instrument according to claim 1, wherein said tool has a length that is less than a full longitudinal length of the molar or premolar to be filled or repaired, such that only one of the mesio-occlusal surface or the disto-occlusal surface is shaped thereby.

6. The instrument according to claim 5, wherein the length of the tool extends from a respective occlusal edge bead to approximately a center of said occlusal part.

7. The instrument according to claim 1, wherein an outer edge of the cavity is defined by the matrix band and the tool gives the composite material an anatomically correct shape up to the matrix band.

8. An instrument for shaping and curing composite material in a temporary cavity that has been established by a matrix band placed around an occlusal part of a molar or premolar to be filled or repaired with the aid of a matrix holder, said instrument comprising a handle with a tool at each end thereof, a first tool having a shaping surface with a shape that corresponds to a mesio-occlusal surface of a molar or premolar of average shape and size generally corresponding with the molar or premolar to be filled or repaired, and a second tool having a shaping surface with a shape that corresponds to a disto-occlusal surface of a molar or premolar of average shape and size generally corresponding with the molar or premolar to be filled or repaired.

9. The instrument according to claim 8, wherein each of said first and second tools has a length that is less than a full longitudinal length of the molar or premolar to be filled or repaired, such that use of the tools shapes only a respective mesio-occlusal or disto-occlusal surface of said molar or premolar to be filled or repaired.

10. The instrument according to claim 9, wherein the length of each tool extends from a respective mesio or disto-occlusal edge bead to approximately a center of the occlusal part of the molar or premolar being filled or repaired.

11. The instrument according to claim 8, wherein an outer edge of the cavity is defined by the matrix band and the tool gives the composite material an anatomically correct shape up to the matrix band.

12. The instrument according to claim 8, wherein the shape of the shaping surface of said first tool corresponds to the mesio-occlusal surface of an upper jaw premolar, and the shape of the shaping surface of said second tool corresponds to the disto-occlusal surface of an upper jaw premolar.

13. The instrument according to claim 8, wherein the shape of the shaping surface of said first tool corresponds to the mesio-occlusal surface of a lower jaw premolar, and the shape of the shaping surface of said second tool corresponds to the disto-occlusal surface of a lower jaw premolar.

14. The instrument according to claim 8, wherein the shape of the shaping surface of said first tool corresponds to the mesio-occlusal surface of a molar, and the shape of the shaping surface of said second tool corresponds to the disto-occlusal surface of a molar.

15. A method of filling or repairing an occlusal surface on a molar, comprising the steps of:
   placing around the molar a flexible matrix band which defines a cavity together with the molar;
   placing a light-hardenable composite material in the cavity;
   working the composite material with a tool that is transparent to light and which has a composite-shaping surface corresponding in shape and size to one of a mesio-occlusal or a disto-occlusal surface of a molar of average shape and size which generally corresponds with the molar to be filled or repaired, said step of working including, pressing said composite-shaping surface against a corresponding mesio or distal part of the matrix band in a direction toward a tooth that lies immediately adjacent the molar being filled or repaired; and pressing down and holding said composite-shaping surface into the composite material and pressed against the matrix band until the composite material is hardened as a result of light radiating through the tool.

16. The method according to claim 15, wherein the tool has a composite-shaping surface corresponding in shape and size to a mesio-occlusal surface and said tool is pressed down in the composite material into contact with at least one of a lingual-palatinal cusp and a disto-occlusal cusp adjacent a mesio-occlusal edge bead.

17. The method according to claim 13, wherein the tool has a composite-shaping surface corresponding in shape and size to a disto-occlusal surface and said tool is pressed down in the composite material into contact with at least one of a lingual-palatinal cusp and a disto-occlusal cusp adjacent a disto-occlusal edge bead.

18. The instrument according to claim 13, wherein an outer edge of the cavity is defined by the matrix band and the tool, when pressed against the matrix band, gives the composite material an anatomically correct shape up to the matrix band.

\* \* \* \* \*